United States Patent [19]
Yukawa et al.

[11] Patent Number: 6,059,946
[45] Date of Patent: May 9, 2000

[54] BIOSENSOR

[75] Inventors: Keiko Yukawa, Nara; Toshihiko Yoshioka; Shiro Nankai, both of Hirakata, all of Japan

[73] Assignee: Matsushita Electric Industrial Co., Ltd., Osaka-fu, Japan

[21] Appl. No.: 09/058,800

[22] Filed: Apr. 13, 1998

[30] Foreign Application Priority Data

Apr. 14, 1997 [JP] Japan .................................. 9-095495
Nov. 14, 1997 [JP] Japan .................................. 9-313653

[51] Int. Cl.$^7$ .................................................. G01N 27/26
[52] U.S. Cl. ............................................ 204/403; 435/817
[58] Field of Search ........................ 204/403; 205/777.5; 435/817

[56] References Cited

FOREIGN PATENT DOCUMENTS

| | | |
|---|---|---|
| 0502504 | 3/1992 | European Pat. Off. . |
| 0735363 | 10/1992 | European Pat. Off. . |
| 0636879 | 7/1994 | European Pat. Off. . |
| 0636879 A2 | 1/1995 | European Pat. Off. . |
| 0744466 | 5/1996 | European Pat. Off. . |

OTHER PUBLICATIONS

JAPIO abstract of Mariko et al. (JP 02102448), Apr. 1990.
CAPLUS abstract of MAriko et al. (JP 02102448), Apr. 1990.
Kazunobou Matsushita, et al., : Bacterial Quinoproteins Glucose Dehydrogenase and Alcohol Dehydrogenase; Principles and Applications of Quinoproteins, edited by Victor L. Davidson, 1993 by Marcel Dekker, Inc; pp. 47–63.

*Primary Examiner*—T. Tung
*Assistant Examiner*—Alex Noguerda
*Attorney, Agent, or Firm*—McDermott, Will & Emery

[57] ABSTRACT

The present invention provides a stable and cost-effective biosensor. The biosensor includes an electrically insulating base plate, an electrode system that includes at least a working electrode and counter electrode formed on the base plate, a reaction layer containing at least an enzyme, an electron acceptor that is formed on, or in the vicinity of, the electrode system, and a divalent water-soluble metallic salt provided in, or in the vicinity of, the reaction layer.

6 Claims, 7 Drawing Sheets

BIOSENSOR

BACKGROUND OF THE INVENTION

The present invention relates to a biosensor facilitating simple and prompt quantitation of a specific component contained in a sample with high accuracy.

Conventionally, various biosensors have been proposed to make simple quantitation of a specific component contained in a sample without the need of dilution or agitation of a sample solution. The following is one example of such biosensor (Japanese Laid-Open Patent Publication Hei 2-062952).

The biosensor disclosed in this reference is produced by the steps of forming an electrode system including a working electrode and a counter electrode on an electrically insulating base plate using a screen printing method or the like and subsequently forming immediately above this electrode system an enzyme reaction layer including a hydrophilic polymer, an oxidoreductase and an electron acceptor. The enzyme reaction layer may further contain a buffer if occasion demands.

When the biosensor thus produced is added with a drop of a sample solution containing a substrate over the enzyme reaction layer, dissolution of the enzyme reaction layer in the sample solution will occur, which triggers a reaction between the enzyme and the substrate thereby causing reduction of the electron acceptor. Upon completion of enzyme reaction, the reduced electron acceptor is oxidized electrochemically. From the oxidation current value measured during this oxidizing step, the concentration of the substrate in the sample solution can be quantitated.

The biosensor as described above permits measurements of various materials in principle if a suitable enzyme corresponding to the substrate of a target material is selected. Enzymes, which normally contain protein as their main component, are often purified before their use in a sensor. Depending on the condition of purification, separation of metallic ion, which is a major active constituent of an enzyme, may occur, causing a change of the cubic structure of the enzyme. As a result, the enzyme may be changed in its substrate specificity or lose its activity.

Moreover, degeneration of the enzyme may occur during preservation of the sensor including the enzyme due to absorption of water in the atmosphere. Therefore, in determining the amount of enzyme to be contained in the reaction layer, the amount of loss due to possible degeneration during preservation must be taken into account.

On the other hand, in such a biosensor whose enzyme reaction is dependent on the amount of the enzyme contained in the reaction layer, responsive current values measured are not proportional to the concentration of the substrate. Therefore, it is required for the reaction layer to contain a sufficient amount of enzyme which is enough to effect a reaction with the target substrate in the sample solution.

As such, at production of a sensor, it is necessary to include in the reaction layer considerably excess amounts of enzyme than the amount of the substrate which is anticipated to exist in the sample solution. Accordingly, the required amount of enzyme per sensor is assumed to become great, which results in a significant increase of the cost per sensor.

BRIEF SUMMARY OF THE INVENTION

The object of the present invention is to provide a cost-effective biosensor with high stability after preservation by causing the enzyme carried on the sensor to exert its maximal activity thereby reducing the amount of enzyme carried per sensor.

The present invention provides a biosensor comprising an electrically insulating base plate, an electrode system including at least a working electrode and a counter electrode formed on the base plate, a reaction layer containing at least an enzyme and an electron acceptor which is formed on or in the vicinity of the electrode system, and a divalent water-soluble metallic salt provided locally in the reaction layer or in an area in the vicinity of the reaction layer, being kept apart from the reaction layer.

In a preferred mode of the present invention, the biosensor comprises an electrically insulating base plate, an electrode system including at least a working electrode and a counter electrode formed on the base plate, a cover member which is integrated into the base plate so as to form a sample supply pathway for supplying a sample to the electrode system between the cover member and the base plate, a reaction layer containing at least an enzyme and an electron acceptor which is formed on or in the vicinity of the electrode system, and a divalent water-soluble metallic salt provided locally in the reaction layer or in an area in the sample supply pathway, the area being kept apart from the reaction layer.

In another preferred mode of the present invention, the metallic salt is isolated from the reaction layer of the biosensor.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
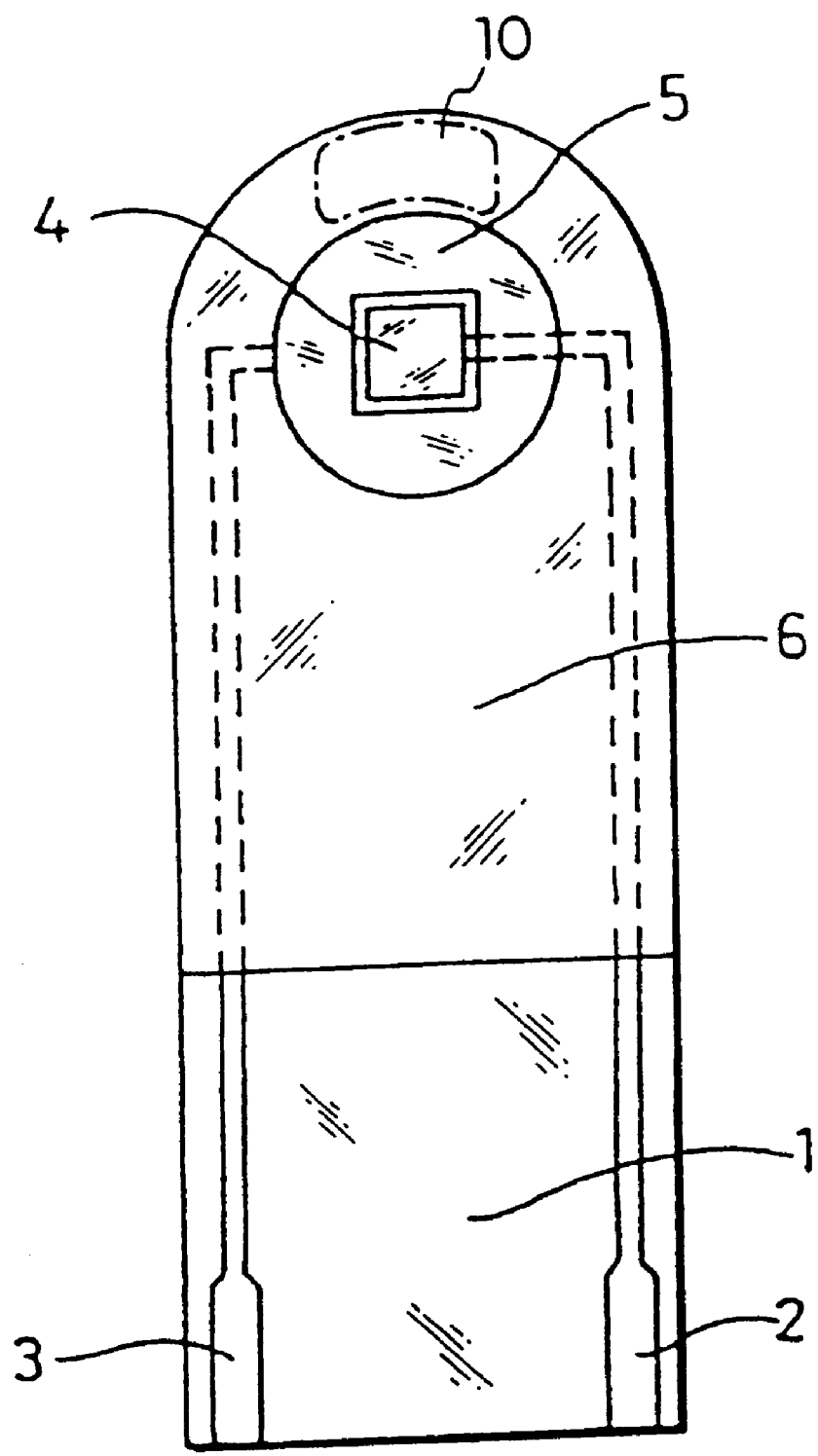
FIG. 1 is a rough plan view of a biosensor in accordance with one example of the present invention with an omission of the reaction layer.

As illustrated above, the biosensor in accordance with the present invention is provided with a divalent water-soluble metallic salt inside or in the vicinity of the reaction layer.

Upon dropping a sample solution such as blood on the sensor, in the presence of a metallic salt inside the sample supply pathway, the sample solution is carried toward the reaction layer while dissolving the metallic salt. When the metallic salt is present in the reaction layer, it is dissolved in the sample solution upon its arrival at the reaction layer. The metallic salt thus dissolved is dissociated to form divalent metallic ion. Then, there occurs an intake of the resultant metallic ion into the enzyme from which metallic ion has been detached during the previous purification process or long-term preservation. As a result, the enzyme resumes its original cubic structure and recovers its enzyme activity. As such, since the activity of the enzyme contained in the reaction layer is promoted, it is possible to minimize the amount of enzyme carried on the sensor, enabling production of a cost-effective sensor.

A preferable metallic salt for such purpose is at least one selected from the group consisting of calcium salt, cadmium salt, manganese salt, magnesium salt and strontium salt. Those salts are preferably chlorides, nitrates or sulfates of the above exemplified metals.

The enzyme which resumes its original structure and recovers its enzyme activity with the aid of the above-mentioned metallic salts may be exemplified as dehydrogenases and oxidases. Of various dehydrogenases, glucose dehydrogenase in particular can produce a better response characteristic because this enzyme manifests improved enzyme activity upon addition of divalent metallic ion, particularly calcium ion. Fructose dehydrogenase can also produce a good response. As the oxidase, glucose oxidase is preferred.

Most of the above-exemplified metallic salts are hygroscopic. When a hygroscopic metallic salt is carried in the reaction layer or on the surface of the reaction layer of a sensor, partial dissolution of the reaction layer may sometimes take place during preservation of the sensor due to dissolution of the metallic salt by absorbing therein water in the air. As a result, the enzyme contained in the reaction layer becomes unstable and degenerative, causing a loss of its enzyme activity. Therefore, it is better to provide the metallic salt so as to keep it apart from the reaction layer. This configuration is effective to increase the reliability of the sensor due to preservation even in a humid atmosphere. However, when it is assumed that the sensor is stored in an absolutely water-free atmosphere, for example, storage being enveloped in a gas-tight film such as aluminum laminated resin film, the metallic salt may coexist with the reaction layer. As discussed above, the determination as to whether the metallic salt should exist inside the reaction layer or in an area apart from the reaction layer or in both is preferably dependent on the atmosphere where the sensor is expected to be stored.

In addition, in order to facilitate dissolution of the metallic salt upon supply of a sample solution to a sensor, it is preferable to provide the metallic salt in the sensor by using a hydrophilic polymer as its carrier. As the hydrophilic polymer for carrying the metallic salt, carboxymethyl cellulose is preferred because it has high solubility in water. Other preferred hydrophilic polymers may be exemplified as hydroxyethyl cellulose, hydroxypropyl cellulose, methyl cellulose, ethyl cellulose, ethylhydroxyethyl cellulose, carboxymethylethyl cellulose, polyvinyl pyrrolidone, polyvinyl alcohol, polyamine such as polylysine, polystyrene sulfonate, gelatin and its derivatives, polyacrylic acid and its salts, polymethacrylic acid and its salts, starch and its derivatives, a polymer of maleic anhydride or its salts, agarose gel and its derivatives.

The divalent water-soluble metallic salt used in the present invention is preferably contained in an amount to make the concentration of the divalent metal at 0.01 mg to 2 mg/ml upon dissolution of the salt in a sample solution supplied to the sensor. The lower limit of 0.01 mg/ml is the minimum essential concentration for causing a metal, e.g., calcium to bind to the enzyme. At a concentration exceeding the upper limit of 2 mg/ml, on the other hand, it is difficult to cause smooth dissolution of the reaction layer in a sample solution upon introduction of the sample solution into the sensor.

The biosensor in accordance with the present invention is directed to quantitation of a substrate contained particularly in blood. The biosensor for such purpose must carry an enzyme at 1 to 50 $\mu$g/unit area (mm$^2$) of the reaction layer. And, the amount of the divalent water-soluble metallic salt is calculated to be 0.003 to 0.6 $\mu$g/mm$^2$ on the basis of the unit area of the reaction layer.

On the other hand, as shown in the below-mentioned examples in accordance with the present invention, the required amount of the enzyme to be carried on a sensor chip is only 0.01 to 0.5 mg/chip if the biosensor requires about 3 $\mu$l of a sample solution for one measurement. From this, the amount of the divalent water-soluble metallic salt required for this biosensor is 0.03 to 6 $\mu$g/chip.

The reaction layer in accordance with the present invention contains an electron acceptor. As the electron acceptor, at least one selected from the group consisting of ferricyanide ion, p-benzoquinone and its derivatives, phenazine methosulfate, methylene blue, ferrocene and its derivatives is preferred.

The reaction layer may further contain a hydrophilic polymer in addition to an enzyme and an electron acceptor. The presence of a hydrophilic polymer in the reaction layer is effective for preventing possible separation of the reaction layer from the surface of the electrode system. The hydrophilic polymer has an additional preventive effect against crack development on the surface of the reaction layer, which is helpful for imparting enhanced reliability to a biosensor.

As mentioned previously, preferred hydrophilic polymers for such purpose may be exemplified as carboxymethyl cellulose, hydroxyethyl cellulose, hydroxypropyl cellulose, methyl cellulose, ethyl cellulose, ethylhydroxyethyl cellulose, carboxymethylethyl cellulose, polyvinyl pyrrolidone, polyvinyl alcohol, polyamine such as polylysine, polystyrene sulfonate, gelatin and its derivatives, polyacrylic acid and its salts, polymethacrylic acid and its salts, starch and its derivatives, a polymer of maleic anhydride or its salts, agarose gel and its derivatives.

For measurements of the oxidation current, a two-electrode system including only a working electrode and a counter electrode and a three-electrode system further including a reference electrode in addition to the two electrodes may be used. The latter facilitates more accurate measurements.

In the following, the present invention will be described more specifically referring to specific examples.

FIG. 1 shows a rough plan view of a biosensor in accordance with the present invention from which the reaction layer is excluded. A silver paste is printed on an electrically insulating base plate 1 of polyethylene terephthalate by screen printing so as to form leads 2 and 3 on the base plate 1. Subsequently, a carbon paste containing a resin binder is printed on the base plate 1 so as to form a working electrode 4. The working electrode 4 is in contact with the lead 2. Then, an electrically insulating layer 6 is further formed on the base plate 1 by printing thereon an insulating paste. The electrically insulating layer 6 covers the periphery of the working electrode 4 so as to hold the exposed area of the working electrode 4 constant. Thereafter, the carbon paste containing a resin binder is printed on the base plate 1 so as to cause the carbon paste to contact the previously formed lead 3, which formed a ring-like counter electrode 5. In this way, an electrode system including the working electrode and the counter electrode was formed on the base plated 1. Then, a reaction layer is formed on the electrode system. After formation of the reaction layer, a divalent water-soluble metallic salt 10 is provided at least in the reaction layer or in an area kept apart from the reaction layer.

Figure 2:
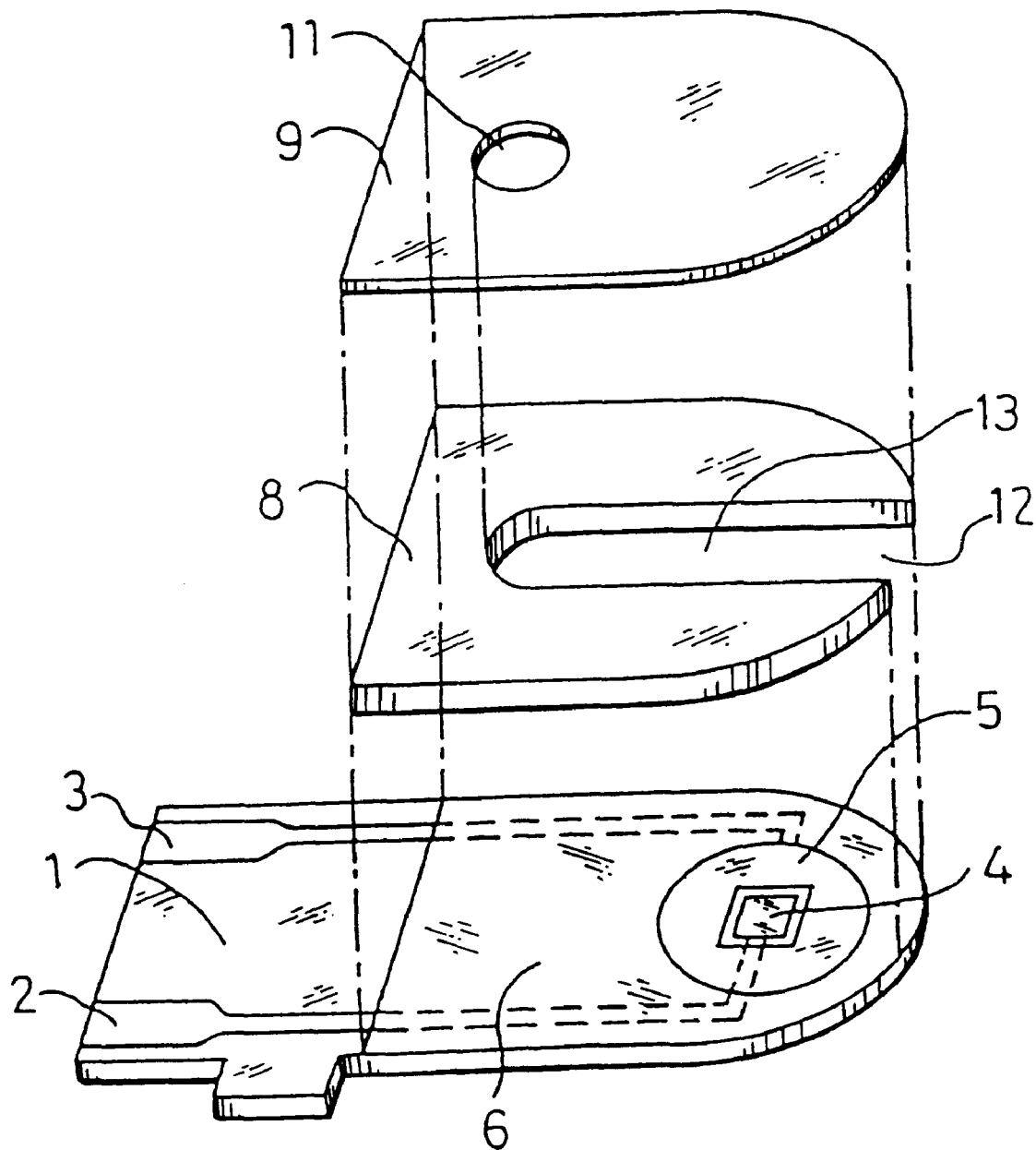
FIG. 2 is an exploded perspective view of a biosensor in accordance with another example of the present invention with an omission of the reaction layer and divalent water-soluble metallic salt.

FIG. 2 shows a broken perspective view of a biosensor in accordance with the present invention from which the reaction layer and the divalent water-soluble metallic salt are excluded. Such biosensor is produced by adhering a spacer 8 and a cover 9 with an air vent 11 to the electrically insulating base plate 1 shown in FIG. 1 in a positional relationship as shown by the dot-dashed line in FIG. 2. A sample supply pathway is formed in a slit 13 of the spacer 8 between the base plate 1 and the cover 9. Numeral 12 designates an opening of the sample supply pathway.

Figure 3:
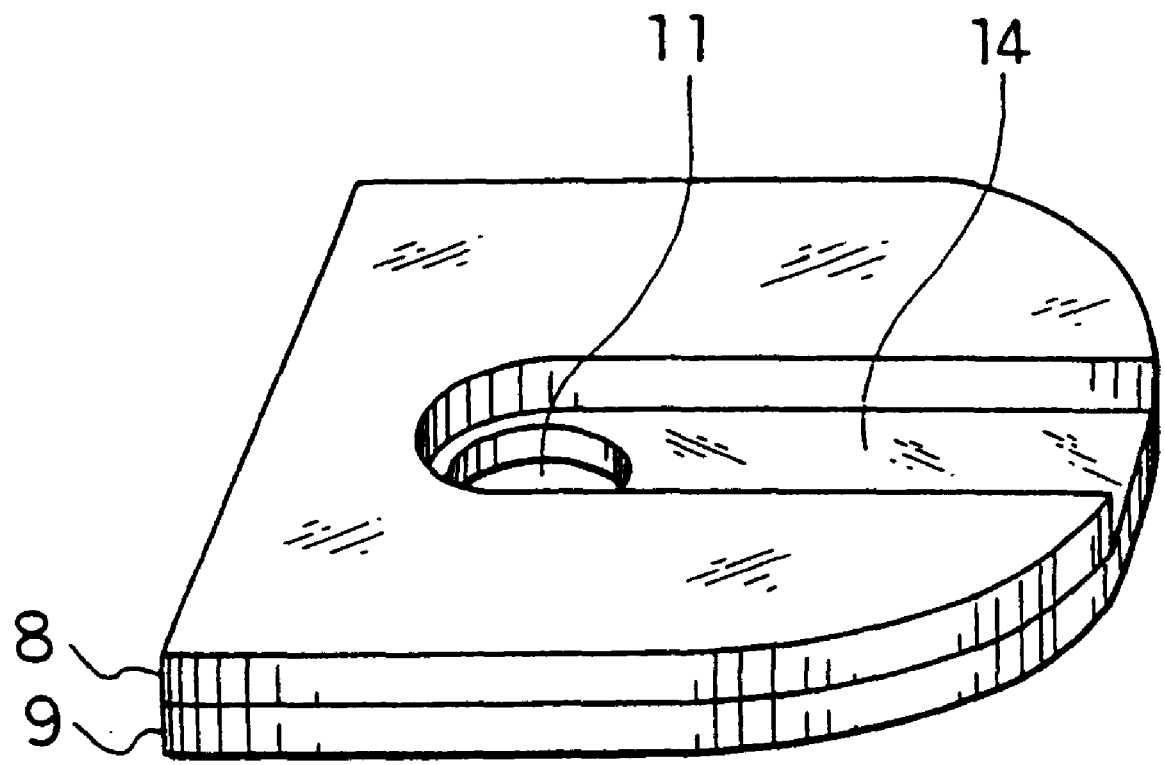
FIG. 3 is a perspective view of the biosensor shown in FIG. 2 with the cover member formed by overlapping a cover over a spacer being arranged upside down.

FIG. 3 shows a perspective view of the biosensor of FIG. 2 showing a cover member formed by overlapping the spacer 8 over the cover 9. In FIG. 3, the arrangement of the spacer 8 and the cover 9 has been turned upside down. Numeral 14 designates a face on the cover 9 which is exposed to a cavity for constituting the sample supply pathway. The reaction layer and/or the salt 10 may be provided on the face where the cover member is exposed to the sample supply pathway.

Figure 4:
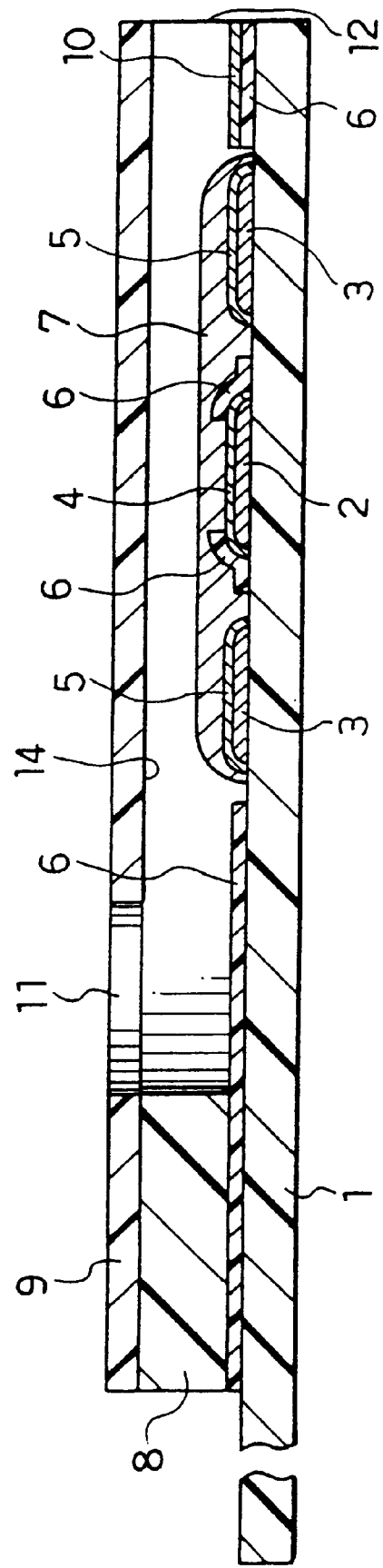
FIG. 4 is a longitudinal cross-sectional view of the vital parts of the biosensor shown in FIG. 2.

FIG. 4 shows a longitudinal cross-sectional view of the vital parts of a biosensor in accordance with the present invention. A reaction layer 7 containing an enzyme and an electron acceptor is formed over the electrically insulating base plate 1 on which the electrode system has previously been formed as shown in FIG. 1. The divalent water-soluble metallic salt 10 is present between the reaction layer 7 and the opening 12 of the sample supply pathway, being kept apart from the reaction layer 7.

EXAMPLE 1

In this example, after the electrode system was formed on the base plate 1 as shown in FIG. 1, 5 μl of a mixed aqueous solution of pyrrolo-quinoline quinone glucose dehydrogenase (hereinafter referred to as "GDH") and potassium ferricyanide was added on the base plate 1 and dried to form thereon the reaction layer 7. The reaction layer thus formed appeared like a disc measuring 3.6 mm in diameter which was almost large enough to cover the electrodes 4 and 5. Separately, a solution containing 5 mg of a divalent water-soluble metallic salt, calcium chloride, was prepared by dissolving it in 10 ml of a 0.5% aqueous solution of carboxymethyl cellulose. Then, 5 μl of the resultant solution was added to the position designated by numeral 10 on the base plate 1 and dried for 10 min in a hot drier at 50° C. so as to carry the divalent water-soluble metallic salt 10 on the base plate 1.

The cover 9 and the spacer 8 were adhered to the resultant base plate 1 in the positional relationship as shown by the dot-dashed line in FIG. 2, which gave a glucose biosensor.

Here, various glucose standard solutions were prepared by varying the glucose concentrations from 0 to 200, 400, 600 and 1000 mg/dl. Each of the glucose standard solutions was supplied to the sensor from the opening 12 of the sample supply pathway. One min after supply of the sample solution, the sensor was applied with a pulse voltage of +0.5 V to the working electrode 4, using the counter electrode 5 as reference. After 5 sec, the current across the working electrode and the counter electrode was measured to evaluate the response characteristic of the sensor. The measurement results are shown by A1 in FIG. 5.

As evident from the figure, the sensor of this example showed a large responsive current value, indicating a high linearity for the correlation between the responsive current value and glucose concentration.

The biosensor produced in this example was stored for 6 months in a humid atmosphere of 20% humidity, and after the storage, the biosensor was evaluated for its response characteristic as a sensor in the same manner as described above. The measurement results are shown by A1b in FIG. 5.

Figure 5:
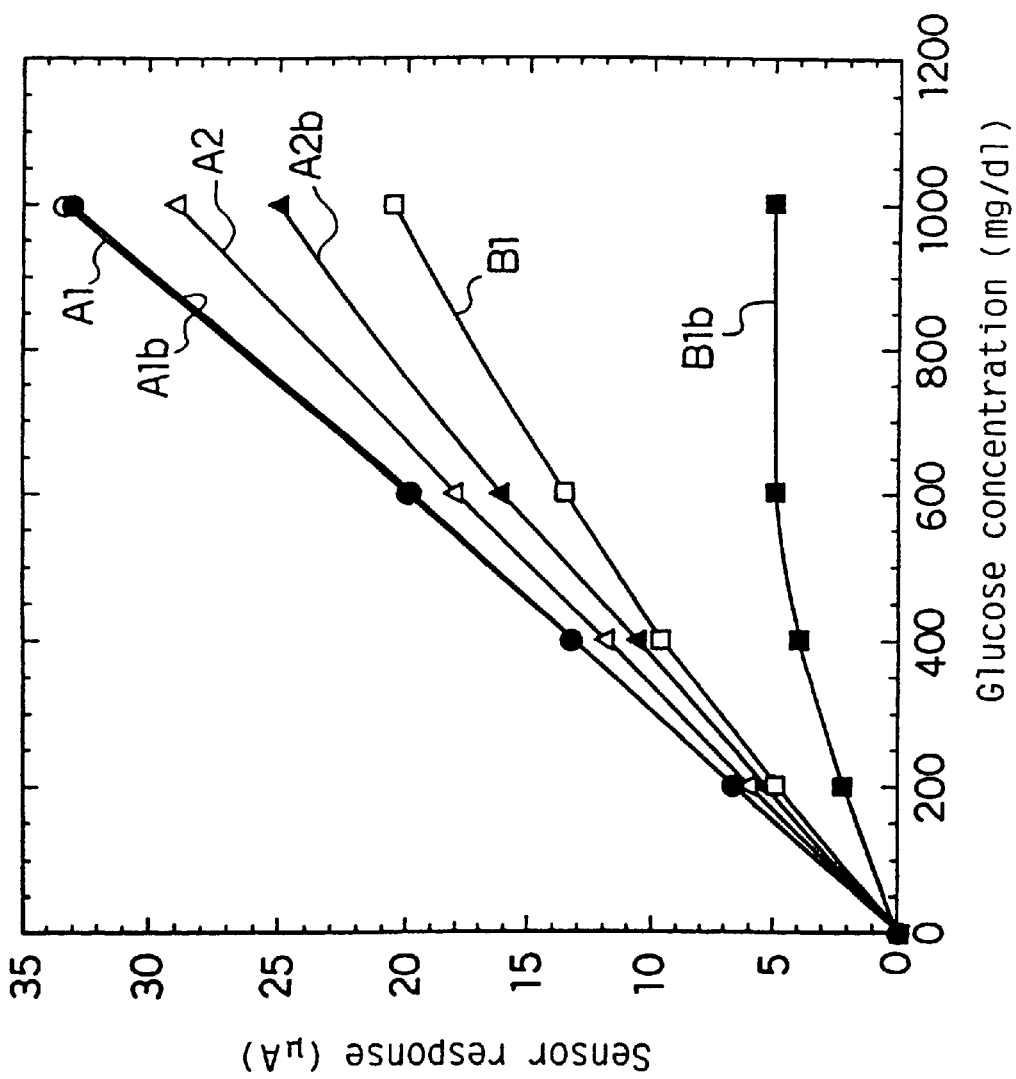
FIG. 5 is a diagram showing a response characteristic to a standard sample solution measured in a biosensor in accordance with one example of the present invention.

As seen from FIG. 5, even after storage, the biosensor was almost unchanged in the response characteristic, compared to that immediately after its production.

COMPARATIVE EXAMPLE 1

Another glucose biosensor was produced in the same manner as in Example 1, except for the absence of the divalent water-soluble metallic salt from the sensor. For comparison, the biosensor was evaluated for its response characteristic as a sensor in the same manner as in Example 1 at two different time points immediately after production of the sensor and after 6-month storage in a 20% humidity atmosphere. The results are shown by B1 and B1b, respectively in FIG. 5.

As apparent from FIG. 5, the responsive current value measured in this comparative example decreased to about 60% of the biosensor of Example 1. Furthermore, the biosensor of the comparative example showed a significant decrease in the responsive current value after 6-month storage, compared to that immediately after production, showing a marked loss of the correlation between the responsive current value and glucose concentration.

EXAMPLE 2

In this example, another glucose biosensor was produced in the same manner as in Example 1, except that the reaction layer was formed by adding a mixed aqueous solution of GDH, potassium ferricyanide and calcium chloride and subsequent drying, and the divalent water-soluble metallic salt was not present alone in the biosensor. The biosensor thus produced was evaluated for its response characteristic as a sensor in the same manner as in Example 1 at two different time points immediately after production and after 6-month storage in a 20% humidity atmosphere. The results are shown by A2 and A2b, respectively in FIG. 5.

As shown in FIG. 5, after 6-month storage, the biosensor of this example showed a decrease in the responsive current value to about 85% of the value immediately after production, and there was a slight reduction in the correlation between the responsive current value and glucose concentration.

EXAMPLE 3

A glucose biosensor was produced in the same manner as in Example 1, except for the use of glucose oxidase (hereinafter referred to as "GOX") as the enzyme. In the biosensor thus produced, its response characteristic as a sensor was evaluated in the same manner as in Example 1 at two different time points immediately after production and after 6-month storage in a 20% humidity atmosphere. The results are shown by A3 and A3b, respectively in FIG. 6.

Figure 6:
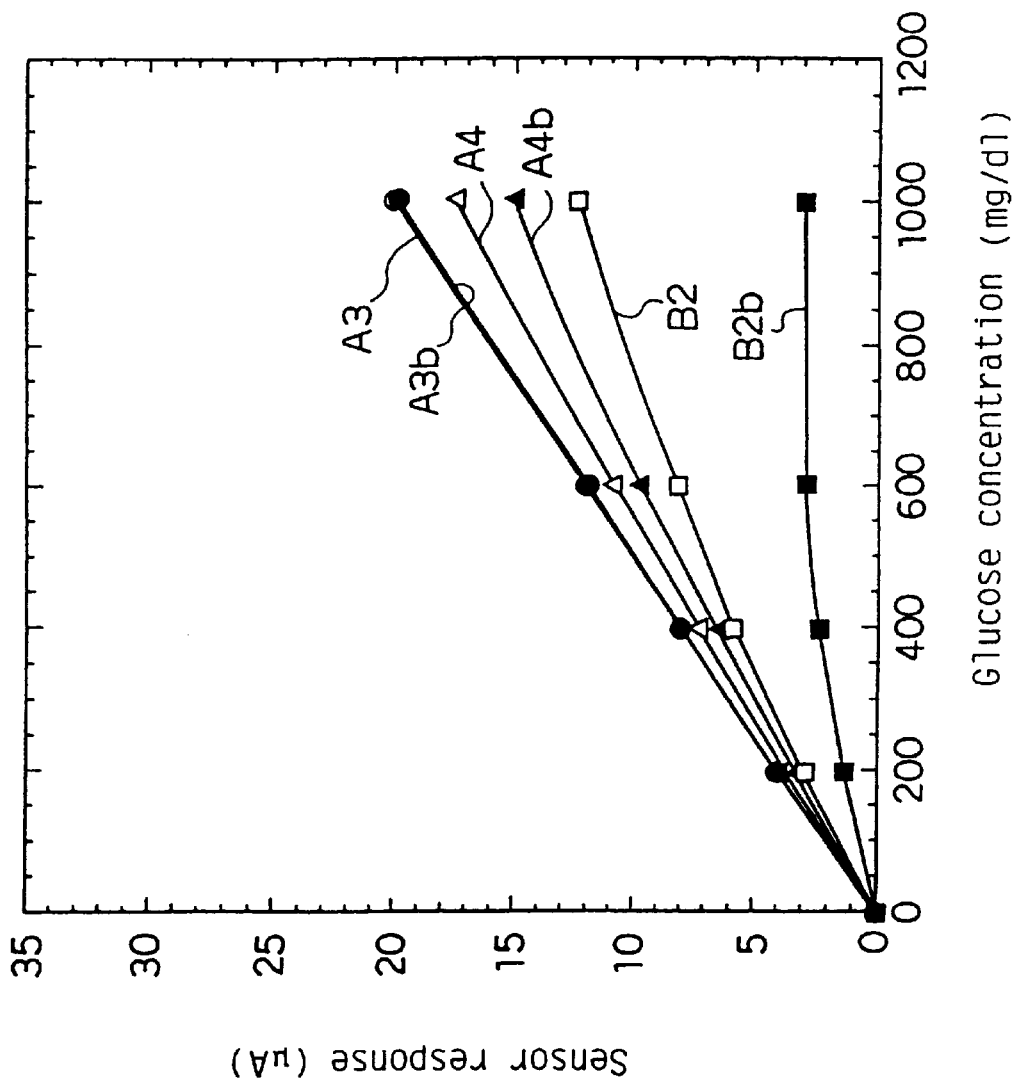
FIG. 6 is a diagram showing a response characteristic to a standard sample solution measured in a biosensor in accordance with another example of the present invention.

As is evident from FIG. 6, the biosensor of Example 3 is exceptional in both the response characteristic and reliability against preservation.

COMPARATIVE EXAMPLE 2

For comparison, another glucose biosensor was produced in the same manner as in Example 3, except for the absence of the divalent water-soluble metallic salt in the sensor. The biosensor thus produced was evaluated for its response characteristic as a sensor in the same manner as in Example 3 at two different time points immediately after production and after 6-month storage in a 20% humidity atmosphere. The results are shown by B2 and B2b, respectively in FIG. 6.

As apparent from FIG. 6, the responsive current value measured in this comparative example decreased to about 60% of the biosensor of Example 3. Furthermore, after 6-month storage, the biosensor of the comparative example showed a significant decrease in the responsive current value compared to that immediately after production, showing a marked loss of the correlation between the responsive current value and glucose concentration.

EXAMPLE 4

In this example, a glucose biosensor was produced in the same manner as in Example 3, except that the reaction layer is formed by adding a mixed aqueous solution of GOX, potassium ferricyanide and calcium chloride and subsequent drying, and the divalent water-soluble metallic salt was not present alone in the biosensor. In the biosensor thus produced, its response characteristic as a sensor was evaluated in the same manner as in Example 3 at two different time points immediately after production and after 6-month storage in a 20% humidity atmosphere. The results are shown by A4 and A4b, respectively in FIG. 6.

As understood from FIG. 6, after 6-month storage, the biosensor of Example 4 showed a decrease in the responsive current value to about 90% of the value immediately after production, and there was a slight reduction in the correlation between the responsive current value and glucose concentration.

EXAMPLE 5

In this example, a biosensor was produced in the same manner as in Example 1, except for the use of fructose dehydrogenase (hereinafter referred to as "FDH") as the enzyme. In the biosensor thus produced, its response characteristic as a sensor was evaluated in the same manner as in Example 1 at two different time points immediately after production and after 6-month storage in a 20% humidity atmosphere, except for the use of a fructose standard solution as standard. The results are shown by A5 and A5b, respectively in FIG. 7.

Figure 7:
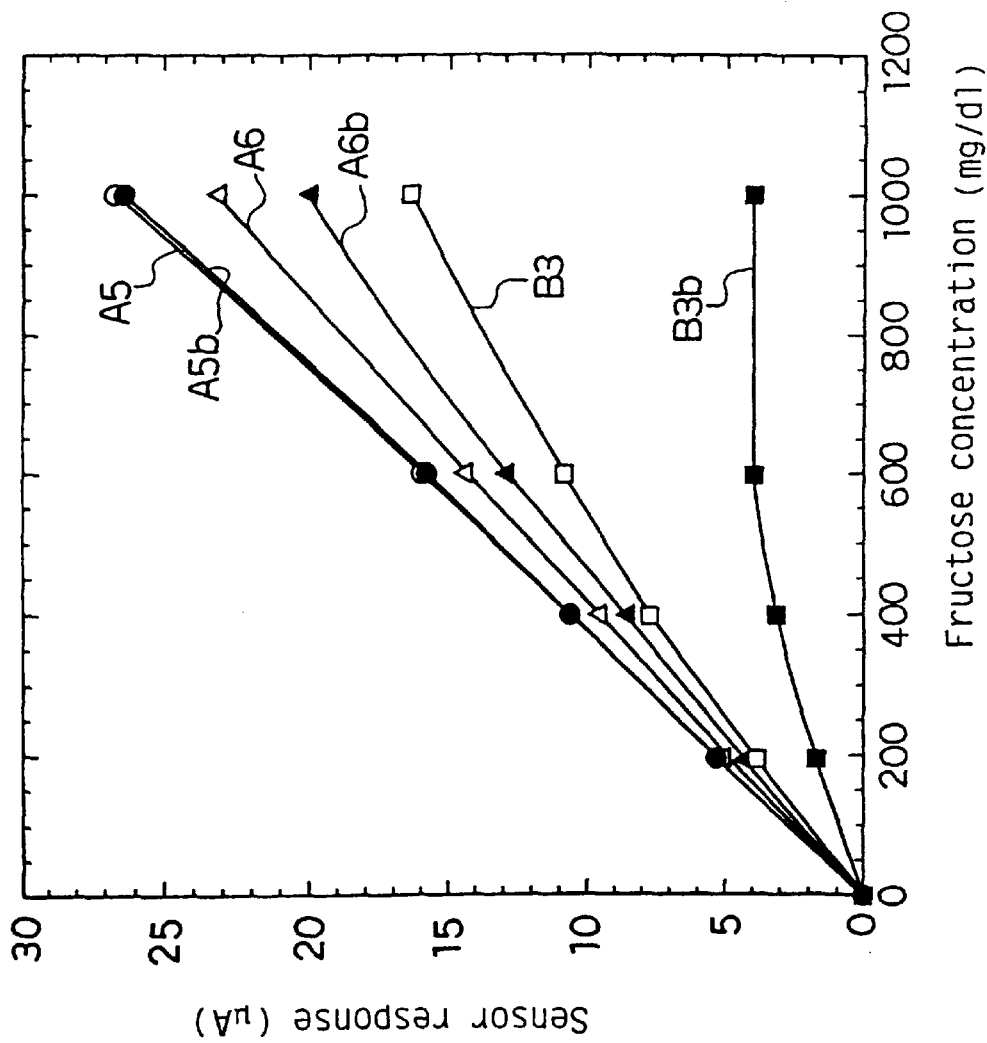
FIG. 7 is a diagram showing a response characteristic to a standard sample solution measured in a biosensor in accordance with still another example of the present invention.

As is evident from FIG. 7, the fructose biosensor of Example 5 is exceptional in both the response characteristic and reliability against preservation.

COMPARATIVE EXAMPLE 3

For comparison, another fructose biosensor was produced in the same manner as in Example 5, except for the absence of the divalent water-soluble metallic salt from the sensor. The biosensor thus produced was evaluated for its response characteristic as a sensor in the same manner as in Example 5, at two different time points immediately after production and after 6-month storage in a 20% humidity atmosphere. The results are shown by B3 and B3b, respectively in FIG. 7.

As apparent from FIG. 7, the biosensor of this comparative example showed a decrease in the responsive current value to about 65% of the biosensor of Example 5. Furthermore, the responsive current value of the sensor after 6-month storage decreased significantly compared to the value immediately after production, showing a marked loss of the correlation between the responsive current value and fructose concentration.

EXAMPLE 6

In this example, another fructose biosensor was produced in the same manner as in Example 5, except that the reaction layer was formed by adding a mixed aqueous solution of FDH, potassium ferricyanide and calcium chloride and subsequent drying, and the divalent water-soluble metallic salt was not present alone in the sensor. In the biosensor thus produced, its response characteristic as a sensor was evaluated in the same manner as in Example 5 at two different time points immediately after production of the sensor and after 6-month storage in a 20% humidity atmosphere. The results are shown by A6 and A6b, respectively in FIG. 7.

As understood from FIG. 7, in the biosensor of Example 6, the responsive current value after 6-month storage decreased to about 85% of the value immediately after production of the sensor, and there was a slight reduction in the correlation between the responsive current value and fructose concentration.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A biosensor comprising:
   an electrically insulating base plate,
   an electrode system including at least a working electrode and a counter electrode formed on said base plate,
   a reaction layer comprising pyrrolo-quinoline quinone glucose dehydrogenase and an electron acceptor which is formed on or in the vicinity of said electrode system, and
   a divalent water-soluble metallic salt provided locally at least in said reaction layer or in an area in the vicinity of said reaction layer, said area being kept apart from said reaction layer,
      wherein said divalent water-soluble metallic salt is selected from the group consisting of calcium salt, cadmium salt, manganese salt and strontium salt.

2. The biosensor in accordance with claim 1, wherein said divalent water-soluble metallic salt is carried in a hydrophilic polymer provided in said area being kept apart from said reaction layer.

3. The biosensor in accordance with claim 1, wherein said enzyme is carried in said reaction layer at 1to 50 $\mu$g/unit area (mm$^2$) and the amount of said divalent water-soluble metallic salt is at 0.003 to 0.6 $\mu$g/mm$^2$ of the unit area of said reaction layer.

4. A biosensor comprising:

an electrically insulating base plate, an electrode system including at least a working electrode and a counter electrode formed on said base plate, a cover member which is integrated into said base plate so as to form a sample supply pathway for supplying a sample solution to said electrode system between said cover member and said bas plate, a reaction layer containing comprising pyrrolo-quinoline quinone glucose dehydrogenase and an electron acceptor which is formed on or in the vicinity of said electrode system, and a divalent water-soluble metallic salt provided locally at least in said reaction layer or in an area in said sample supply pathway, said area being kept apart from said reaction layer, wherein said divalent water-soluble metallic salt is selected from the group consisting of calcium salt, cadmium salt, manganese salt, and strontium salt.

5. The biosensor in accordance with claim 4, wherein said divalent water-soluble metallic salt is carried in a hydrophilic polymer provided in said area being kept apart from said reaction layer.

6. The biosensor in accordance with claim 4, wherein said enzyme is carried in said reaction layer at 1 to 50 $\mu$g/unit area (mm$^2$) and the amount of said divalent water-soluble metallic salt is at 0.003 to 0.6 $\mu$g/mm$^2$ of the unit area of said reaction layer.

* * * * *

UNITED STATES PATENT AND TRADEMARK OFFICE
CERTIFICATE OF CORRECTION

PATENT NO. : 6,059,946
DATED : May 09, 2000
INVENTOR(S) : Keiko YUGAWA, et al.

It is certified that error appears in the above-identified patent and that said Letter Patent is hereby corrected as shown below:

On the Title page:

Section [75], change the first inventor's last name from "Yukawa" to --Yugawa--.

Signed and Sealed this

Twenty-fourth Day of April, 2001

Attest:

NICHOLAS P. GODICI

Attesting Officer

Acting Director of the United States Patent and Trademark Office